(12) United States Patent
Hussein et al.

(10) Patent No.: US 10,752,817 B2
(45) Date of Patent: Aug. 25, 2020

(54) HOT-MELT ADHESIVE COMPOSITION FOR ELASTIC ATTACHMENTS

(71) Applicant: BOSTIK SA, La Plaine Saint Denis (FR)

(72) Inventors: Naji Hussein, Compiegne (FR); Severine Beauchet, Antheuil-Portes (FR)

(73) Assignee: BOSTIK SA, La Plaine Saint Denis (FR)

( * ) Notice: Subject to any disclaimer, the term of this patent is extended or adjusted under 35 U.S.C. 154(b) by 326 days.

(21) Appl. No.: 15/298,610

(22) Filed: Oct. 20, 2016

(65) Prior Publication Data

US 2017/0114257 A1    Apr. 27, 2017

(30) Foreign Application Priority Data

Oct. 23, 2015 (EP) .................................... 15306702

(51) Int. Cl.
  *C09J 165/00* (2006.01)
  *B32B 27/32* (2006.01)
  (Continued)

(52) U.S. Cl.
  CPC ........... *C09J 165/00* (2013.01); *A61L 15/225* (2013.01); *A61L 15/585* (2013.01); *B32B 5/022* (2013.01); *B32B 5/26* (2013.01); *B32B 7/12* (2013.01); *B32B 27/06* (2013.01); *B32B 27/12* (2013.01); *B32B 27/32* (2013.01); *C08L 23/06* (2013.01);
  (Continued)

(58) Field of Classification Search
  CPC ..... A61L 15/225; A61L 15/585; B32B 27/06;
  B32B 27/12; B32B 27/32; B32B 5/022;
  B32B 5/26; B32B 7/12; B32B 2250/03;
  B32B 2250/05; B32B 2250/40; B32B
  2255/02; B32B 2255/10; B32B
  2262/0292; B32B 2307/51; B32B
  2307/56; B32B 2307/718; B32B 2555/00;
  B32B 2555/02; C08L 23/06; C08L
  23/0869;
  (Continued)

(56) References Cited

U.S. PATENT DOCUMENTS 6,143,818 A * 11/2000 Wang ....................... C08K 5/01
                                                         524/528
6,747,114 B2 * 6/2004 Karandinos ............ C09J 123/10
                                                         526/348.2

(Continued)

FOREIGN PATENT DOCUMENTS

WO    2011/059431 A1    5/2011
WO    WO-2011059431 A1 *  5/2011  ............ C08L 23/142

OTHER PUBLICATIONS

AC 596 MAPP Data Sheet (Year: 2018).*
(Continued)

*Primary Examiner* — Travis M Figg
(74) *Attorney, Agent, or Firm* — Millen, White, Zelano & Branigan, PC; Ryan Pool

(57) ABSTRACT

The present invention relates to a hot-melt adhesive composition comprising a propylene homopolymer, an alpha-olefin copolymer, a carboxylic acid- and/or anhydride-functionalized olefin compound and a tackifying resin. The present invention also relates to a laminate comprising the hot-melt adhesive composition according to the invention that can be used in disposable hygiene articles.

20 Claims, 6 Drawing Sheets

(51) Int. Cl.

| | |
|---|---|
| *C09J 123/12* | (2006.01) |
| *C08L 23/08* | (2006.01) |
| *B32B 5/26* | (2006.01) |
| *C08L 23/14* | (2006.01) |
| *C08L 23/06* | (2006.01) |
| *B32B 5/02* | (2006.01) |
| *B32B 27/12* | (2006.01) |
| *C08L 51/06* | (2006.01) |
| *A61L 15/22* | (2006.01) |
| *A61L 15/58* | (2006.01) |
| *B32B 7/12* | (2006.01) |
| *B32B 27/06* | (2006.01) |
| *C09J 5/00* | (2006.01) |

(52) U.S. Cl.
CPC ......... *C08L 23/0869* (2013.01); *C08L 23/142* (2013.01); *C08L 23/147* (2013.01); *C08L 51/06* (2013.01); *C09J 5/00* (2013.01); *C09J 123/12* (2013.01); *B32B 2250/03* (2013.01); *B32B 2250/05* (2013.01); *B32B 2250/40* (2013.01); *B32B 2255/02* (2013.01); *B32B 2255/10* (2013.01); *B32B 2262/0292* (2013.01); *B32B 2307/51* (2013.01); *B32B 2307/56* (2013.01); *B32B 2307/718* (2013.01); *B32B 2555/00* (2013.01); *B32B 2555/02* (2013.01); *C09J 2423/00* (2013.01)

(58) Field of Classification Search
CPC ...... C08L 23/142; C08L 23/147; C08L 51/06; C09J 123/12; C09J 165/00; C09J 5/00; C09J 2423/00
See application file for complete search history.

(56) References Cited

U.S. PATENT DOCUMENTS

| | | | |
|---|---|---|---|
| 2004/0220320 A1* | 11/2004 | Abhari | C08F 10/06 524/487 |
| 2007/0135563 A1* | 6/2007 | Simmons | C08L 23/04 524/570 |
| 2009/0203847 A1* | 8/2009 | Ellis | C08L 23/04 525/221 |
| 2010/0069867 A1* | 3/2010 | Noda | B32B 27/32 604/378 |
| 2010/0096074 A1* | 4/2010 | Schoenbeck | B32B 27/08 156/176 |
| 2013/0005884 A1* | 1/2013 | Davis | C08L 23/142 524/275 |
| 2013/0060215 A1* | 3/2013 | Knutson | C08K 5/005 604/366 |
| 2013/0109801 A1* | 5/2013 | Coffey | C09J 123/0869 524/524 |
| 2014/0199545 A1* | 7/2014 | Moriguchi | C09J 11/06 428/349 |
| 2014/0234644 A1* | 8/2014 | Davis | C08L 23/06 428/486 |
| 2015/0166850 A1* | 6/2015 | Tse | C09J 123/06 524/528 |
| 2015/0210902 A1* | 7/2015 | Botros | B32B 7/12 428/355 EN |

OTHER PUBLICATIONS

AC 596 Data Sheet (Year: 2019).*
European Search Report dated Feb. 4, 2016 issued in corresponding EP 15306702 application (2 pages).

* cited by examiner

FIG. 2
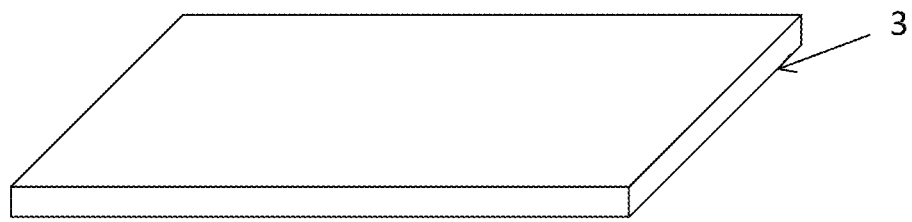
FIG. 2A
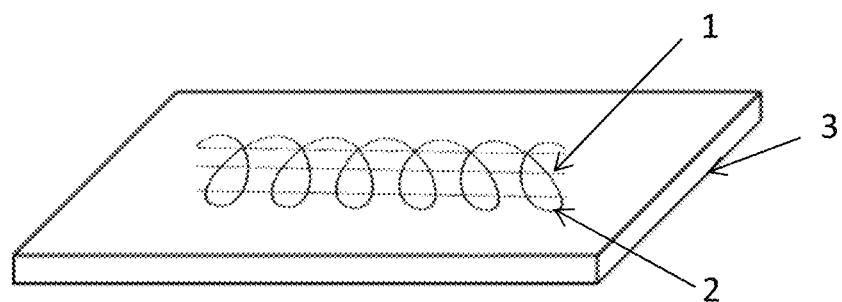
FIG. 2B
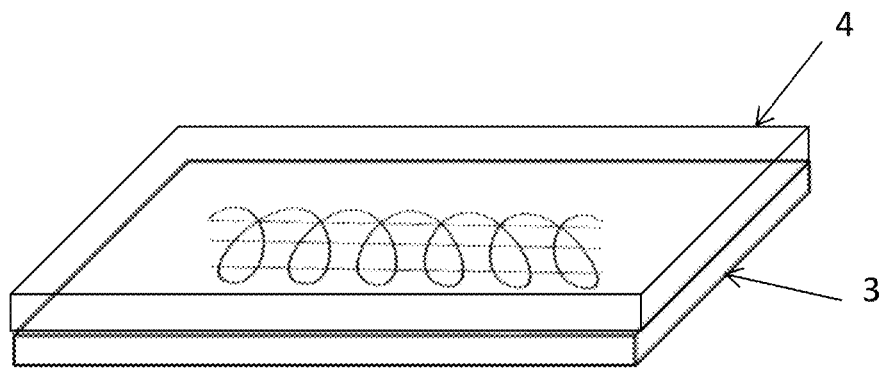
FIG. 2C

HOT-MELT ADHESIVE COMPOSITION FOR ELASTIC ATTACHMENTS

FIELD OF THE INVENTION

The present invention relates to a hot-melt adhesive composition comprising a polypropylene homopolymer, an alpha-olefin copolymer, a carboxylic acid- and/or anhydride-functionalized olefin compound and a tackifying resin. The present invention also relates to a laminate comprising the hot-melt adhesive composition according to the invention that can be used in disposable hygiene articles.

BACKGROUND OF THE INVENTION

Disposable hygiene articles are made from a wide variety of substrates (non-woven, elastomeric material, film, such as polyolefin film and in particular polyethylene or polypropylene film) bonded with adhesive materials. Among examples of disposable hygiene articles, mention may be made of diapers, napkins or adult incontinence disposable articles. The disposable hygiene articles are produced at high speed line rates.

In such production, hot melt adhesives are typically used because they can be easily applied to substrates (at the molten state) and rapidly develop strong bond upon cooling, without any additional manufacturing steps such as solvent removal.

Generally, several kinds of hot melt adhesives can be found in disposable hygiene articles, depending on their emplacement and final function, such as:

Core adhesives: used to keep in place the diaper core (fluff and SuperAbsorbentPolymer "SAP"), during the manufacture of the diaper but also during the use of the diaper mainly after that said diaper has been wet.

Construction adhesives: which bind the polyethylene back sheet to the nonwoven substrates or which bind two nonwoven substrates.

Elastic adhesives: used to bind elastic strands to polyethylene "PE" (or to polypropylene "PP") and Nonwoven substrates.

Styrenic bloc copolymers based adhesive are the main hot melt adhesives used in the absorbing articles industry (core, elastic and construction applications). Over the years, polyolefin based adhesives have been formulated, thanks to development of new polyolefins copolymers (Amorphous Poly-Alpha-Olefins "APAO" by Ziegler-Natta and then by Metallocene catalysis). However, the use of the polyolefin polymers was limited to construction adhesives, because of their poor processability (spraying), lack of cohesion and low creep resistance.

WO 2013/039262 describes a hot-melt adhesive composition comprising a propylene homopolymer and a wax modified with carboxylic acid and/or carboxylic acid anhydride. Said document does not describe the hot-melt adhesive composition of the invention.

In elastic attachment applications, adhesive is generally used to attach elastic material (such as polyurethane based strands) to sheet-like substrates. First, the elastic material is stretched prior to bonding and then adhesive is applied onto the elastics, either by spraying or contact applications, then the elastics coated with the adhesive are quickly laminated between a nonwoven substrate and a polyolefin film. After that, elastics are permitted to relax, creating a gathered (or rushed) laminate having substantial flexibility. The adhesive should maintain the elastics in place, particularly when solicited during manufacturing and use of the disposable hygiene article. This means that an adhesive with high cohesion and elasticity is required. In order to avoid any adhesive failure, good adhesion on the elastic strands is also recommended.

U.S. Pat. No. 6,329,468 describes the use of flexibile polyolefin FPO (based on propylene based polymers having a melt flow rate equal to or greater than 5 g/10 min and a density between 0.860 to 0.900 g/cm$^3$. In U.S. Pat. No. 6,143,818, they also used a blend of ethylene-propylene copolymer and ethylene-propylene-diene monomer terpolymer and semi crystalline polymer. The disclosed hot melt adhesive composition shows good adhesion to a variety of substrates and good sprayability with high creep resistance. However, the application temperature is relatively high (175° C.-176° C.) which may limit the use of these adhesives especially in the case of thin and more sensitive substrates. Indeed, sensitive substrates may burn at high temperatures. Another drawback with the use of high temperatures is that they involve a higher energy consumption.

More recently, US 2010/0305528 describes polyolefins adhesive for elastic attachment applications comprising an ethylene/alpha-olefin copolymer and an acid anhydride modified polyolefin. US 2010/0305528 describes adhesive compositions with balanced properties of cohesive and adhesive strength. Said document has tested the creep resistance of the compositions with a high coating weight of adhesive composition.

Because of the insufficient elastic performances of polyolefin-based adhesive, commercially available elastic adhesives are today limited to styrene block copolymers based adhesive.

There is thus a need to develop adhesive compositions based on polyolefins for elastic attachments.

SUMMARY OF THE INVENTION

A first object of the present invention is a hot-melt adhesive composition comprising:
(A) at least one propylene homopolymer,
(B) at least one alpha-olefin copolymer comprising or not propylene provided that if said alpha-olefin copolymer does not comprise propylene, said alpha-olefin copolymer has a density higher than or equal to 0.890 g/cm3,
(C) at least one carboxylic acid- and/or anhydride-modified polyolefin compound selected from:
(C1) carboxylic acid- and/or anhydride-modified polyolefin copolymer having a molecular weight higher than 10000 g/mol and having a density higher than or equal to 0.890 g/cm3, and
(C2) carboxylic acid- and/or anhydride-modified polyolefin wax having a molecular weight ranging from 100 to 10000 g/mol,
(D) at least one tackifying resin,
being understood that the adhesive composition does not comprise amorphous olefin homopolymers or olefin copolymers.

Preferably, the hot-melt adhesive composition comprises:
(A) from 2 to 40% by weight of at least one propylene homopolymer,
(B) from 2 to 40% by weight of at least one alpha-olefin copolymer comprising or not propylene provided that if said alpha-olefin copolymer does not comprise propylene, said alpha-olefin copolymer has a density higher than or equal to 0.890 g/cm3,
(C) from 1 to 20% by weight of at least one carboxylic acid- and/or anhydride-modified polyolefin compound, and (D) from 10 to 75% by weight of at least one tackifying resin, based on the total weight of the hot-melt adhesive composition.

According to an embodiment of the invention, the mass ratio between the propylene homopolymer (A) and the alpha-olefin copolymer (B) is higher than or equal to 0.8.

Preferably, the alpha-olefin copolymer (B) comprises at least one propylene monomer.

Preferably, the carboxylic acid- and/or anhydride-modified polyolefin compound (C) comprises at least one monomer selected from propylene and ethylene, and at least one monomer selected from butylene, pentene or hexene.

According to an embodiment of the invention, the carboxylic acid- and/or anhydride-modified polyolefin compound (C) comprises from 0.5 to 10% by weight of carboxylic acid and/or anhydride functions, based on the total weight of the carboxylic acid- and/or anhydride-modified polyolefin compound.

According to an embodiment of the invention, the carboxylic acid- and/or anhydride-modified polyolefin compound (C) is selected from a carboxylic acid- and/or anhydride-modified polyolefin copolymer having a molecular weight higher than 10000 g/mol and having a density higher than or equal to 0.890 g/cm3 (C1). Preferably, the hot-melt adhesive further comprises at least one carboxylic acid- and/or anhydride-modified polyolefin wax having a molecular weight ranging from 100 to 10000 (C2).

Another object of the present invention is a laminate comprising at least one elastic material and at least two substrates, said elastic material being inserted between the two substrates and covered with the hot-melt adhesive composition according to the present invention.

Preferably, the adhesive composition is applied in a spiral form onto the elastic material(s).

According to an embodiment of the invention, the adhesive composition is applied in an amount of from 10 to 50 g/m².

According to an embodiment of the invention, one substrate is selected from non-woven materials and a second substrate is selected from polyolefin films.

Another object of the present invention is a process for manufacturing the laminate according to the invention, said process comprising the steps:
  providing a first substrate,
  providing at least one elastic material,
  applying the adhesive composition according to the invention onto at least one elastic material,
  contacting the elastic material(s) covered with the adhesive composition with the first substrate,
  contacting the second substrate with the elastic material(s).

Another object of the present invention is a disposable hygiene article comprising at least one laminate according to the invention.

A further object of the present invention is the use of a hot-melt adhesive composition according to the present invention for binding an elastic material between two separate substrates.

The composition according to the present invention can bond elastic strands in disposable hygiene articles.

The composition according to the present invention can be applied at a temperature less than 160° C., in particular at a temperature of about 150° C.

The composition according to the present invention provides a bonding of the strands having a good creep resistance and a good ageing, even at high temperature (such as 55° C.).

The bonding obtained with the composition according to the present invention can be stored during several days or even several weeks without losing its performances.

The composition according to the present invention can be applied either by contact application or by spraying application.

The composition according to the present invention may be applied with a low coating weight (such as 15 g/m²) while obtaining fulfilling creep resistance.

The composition according to the present invention allows providing performances that are similar to the performances that can be obtained with adhesive compositions based on styrenic-bloc copolymers.

Further features and advantages of the invention will appear from the following description of embodiments of the invention, given as non-limiting examples.

BRIEF DESCRIPTION OF THE DRAWINGS

FIG. 2 illustrates a process for manufacturing a laminate according to the invention comprising two substrates (3, 4), elastic materials (1) covered with an adhesive composition (2). FIG. 2A shows one substrate (3), FIG. 2B shows one substrate (3) and elastic materials (1) covered with an adhesive composition (2) and FIG. 2C shows a laminate comprising two substrates (3, 4), and elastic materials (1) covered with an adhesive composition (2).

FIG. 3A and FIG. 3B illustrate the case wherein the adhesive composition has been applied on the elastic materials using a contact application.

FIG. 4A and FIG. 4B illustrate the case wherein the adhesive composition has been applied on the elastic materials using a spiral application.

DETAILED DESCRIPTION OF THE INVENTION

Figure 1A:
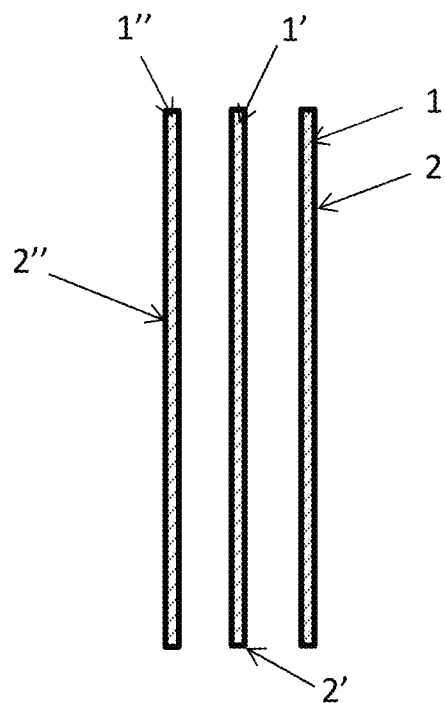
FIG. 1A shows three elastic strands (1, 1', 1'') covered with the adhesive composition according to the invention (2, 2', 2'') using a contact application.

The present invention is directed to a hot-melt adhesive composition comprising:
  at least one propylene homopolymer (hereinafter noted A),
  at least one alpha-olefin copolymer comprising or not propylene provided that if said alpha-olefin copolymer does not comprise propylene, said alpha-olefin copolymer has a density higher than or equal to 0.890 g/cm³ (hereinafter noted B),
  at least one carboxylic acid- and/or anhydride-modified polyolefin compound C selected from:
    carboxylic acid- and/or anhydride-modified polyolefin copolymer having a molecular weight higher than 10000 g/mol and having a density higher than or equal to 0.890 g/cm³ (hereinafter noted C1), and carboxylic acid- and/or anhydride-modified polyolefin wax having a molecular weight ranging from 100 to 10000 g/mol (hereinafter noted C2), at least one tackifying resin (hereinafter noted D), being understood that the adhesive composition does not comprise amorphous olefin homopolymers or olefin copolymers.

According to an embodiment of the invention, the hot-melt adhesive composition comprises:

from 2 to 40% by weight, preferably from 4 to 30% by weight, more preferably from 5 to 20% by weight, of at least one propylene homopolymer A, from 2 to 40% by weight, preferably from 4 to 30% by weight, more preferably from 5 to 20% by weight, of at least one alpha-olefin copolymer B, from 1 to 20% by weight, preferably from 3 to 15% by weight, more preferably from 5 to 10% by weight, of at least one carboxylic acid- and/or anhydride-modified polyolefin compound C, and from 10 to 75% by weight, preferably from 20 to 70% by weight, more preferably from 30 to 65% by weight, of at least one tackifying resin D, based on the total weight of the hot-melt adhesive composition.

Ingredient A

By "propylene homopolymer" it is to be understood a polymer consisting essentially in propylene monomer units. Preferably, the propylene homopolymer A does not comprise any grafts and/or modifications by any functional groups.

According to an embodiment, the propylene homopolymer A used in the composition of the invention has a Ring and Ball Softening point higher than 100° C., preferably higher than or equal to 105° C., more preferably higher than or equal to 110° C., even more preferably higher than or equal to 115° C., still more preferably higher than or equal to 120° C. According to an embodiment, the Ring and Ball Softening point of the propylene homopolymer A is less than or equal to 200° C., preferably less than or equal to 175° C., more preferably less than or equal to 140° C., even more preferably less than or equal to 135° C.

In the present invention, the Ring and Ball Softening point of the homopolymer of propylene is measured according to ASTM E-28-99 standard.

The propylene homopolymer A that can be used in the adhesive composition of the present invention may be obtained according to the method described in paragraphs [0037] to [0044] of the document US 2004/0039117.

According to an embodiment, the propylene homopolymer A used in the adhesive composition of the invention has a molecular weight ranging from 30000 to 200000 g/mol, preferably from 40000 to 170000 g/mol, in particular from 100000 to 150000 g/mol.

The molecular weight may be measured according to any known methods for the skilled person. For example, the molecular weight may be measured by Gel Permeation Chromatography (GPC).

An example of propylene homopolymer A that can be used in the present invention is the L-Modu® 5901 (available from Idemitsu Chemicals).

According to an embodiment, the propylene homopolymer(s) A represent from 2 to 40% by weight, preferably from 4 to 30% by weight, more preferably from 5 to 20% by weight, of the total weight of the adhesive composition.

Ingredient B

By "alpha-olefin copolymer B" or "unmodified alpha-olefin copolymer B", it is to be understood a copolymer consisting essentially in alpha-olefin monomers. Preferably, the alpha-olefin copolymer used in the composition of the invention does not comprise any grafts. In particular, the alpha-olefin copolymer is not modified by carboxylic acid and/or anhydride functions.

By "alpha-olefin" it is to be understood an olefin comprising a double bond carbon-carbon in terminal (or alpha) position.

According to an embodiment of the invention, the alpha-olefin copolymer B comprises at least propylene monomers. Preferably, the alpha-olefin copolymer B comprises at least 50% by weight, more preferably at least 60% by weight, even more preferably at least 70% by weight of propylene, based on the total weight of the alpha-olefin copolymer.

According to an embodiment, the alpha-olefin copolymer B is a terpolymer, i.e. comprises three different monomers, preferably one of the three monomers is propylene monomer.

When the unmodified alpha-olefin copolymer B does not comprise propylene monomers, the density of said unmodified alpha-olefin copolymer is higher than or equal to 0.890 g/cm³, preferably higher than or equal to 0.900 g/cm³, more preferably higher than 0.910 g/cm³. Preferably, when the unmodified alpha-olefin copolymer B comprises less than 30% by weight or less than 40% by weight or less than 50% by weight of propylene monomers, based on the total weight of the alpha-olefin copolymer, the density of said unmodified alpha-olefin copolymer B is higher than or equal to 0.890 g/cm³, preferably higher than or equal to 0.900 g/cm³, more preferably higher than 0.910 g/cm³.

Preferably, the unmodified alpha-olefin copolymer B comprises alpha-olefin monomers having from 2 to 16 carbon atoms, preferably from 2 to 8 carbon atoms.

According to an embodiment, the unmodified alpha-olefin copolymer B comprises at least one propylene monomer and at least one other alpha-olefin monomer selected from ethylene, butylene, pentene, hexene.

According to an embodiment of the invention, the unmodified alpha-olefin copolymer B has a molecular weight ranging from 20000 to 200000 g/mol.

According to an embodiment of the invention, the mass ratio between the propylene homopolymer A and the alpha-olefin copolymer(s) B used in the adhesive composition is higher than or equal to 0.8, preferably higher than or equal to 0.9, more preferably higher than or equal to 1.

Among "unmodified" alpha-olefin copolymers B that can be used in the present invention, mention may be made of Tafmer® PN20300 or Tafmer® PN2070 (available from Mitsui Chemicals).

According to an embodiment, the alpha-olefin copolymer(s) B represent from 1 to 25% by weight, preferably from 2 to 20% by weight, more preferably from 3 to 15% by weight, even more preferably from 4 to 10% by weight, of the total weight of the adhesive composition.

Ingredient C

By "carboxylic acid- and/or anhydride-modified polyolefin compound C" or "modified polyolefin compound C" it is to be understood a polyolefin copolymer or wax comprising at least one olefin monomer, said polyolefin copolymer or wax is modified with carboxylic acid functions and/or carboxylic anhydride functions.

The carboxylic acid- and/or anhydride-modified polyolefin compound C used in the adhesive composition of the invention is selected from:

carboxylic acid- and/or anhydride-modified polyolefin copolymer having a molecular weight higher than 10000 g/mol and having a density higher than or equal to 0.890 g/cm$^3$ (hereafter noted C1), and carboxylic acid- and/or anhydride-modified polyolefin wax having a molecular weight ranging from 100 to 10000 g/mol (hereafter noted C2).

According to an embodiment, the modified polyolefin compound C comprises at least one monomer selected from propylene and ethylene, and at least one other monomer selected from butylene, pentene or hexene. Preferably, the modified polyolefin compound C comprises from 50 to 98%, preferably from 60 to 95% by weight of ethylene or propylene monomer and from 2% to 50%, preferably from 5 to 40% by weight of at least one other monomer selected from butylene, pentene or hexene, based on the total weight of the polyolefin copolymer.

The modified polyolefin compound C is modified by carboxylic acid or anhydride functions, in particular the chain of the polyolefin compound may be grafted by carboxylic acid and/or anhydride functions. The grafting may be made by processes known to the skilled person, for example the grafting may be made by reactive extrusion.

Preferably, the carboxylic acid- and/or anhydride-modified polyolefin compound C comprises from 0.5 to 10% by weight, preferably from 1 to 5% by weight of carboxylic acid and/or anhydride functions, based on the total weight of the carboxylic acid- and/or anhydride-modified polyolefin compound.

According to an embodiment of the invention, the carboxylic acid- and/or anhydride-modified polyolefin compound C consists essentially in olefin monomers and carboxylic acid- and/or anhydride-derived monomer and/or grafts.

According to an embodiment of the invention, the carboxylic acid and/or anhydride functions are selected from dicarboxylic acid or anhydride functions. Preferably, the carboxylic acid and/or anhydride functions are selected from maleic acid, maleic anhydride, fumaric acid, succinic acid, succinic anhydride, phthalic acid, phthalic anhydride, glutaric acid, glutaric anhydride, itaconic acid, acrylic acid or methacrylic acid. More preferably, the carboxylic acid and/or anhydride functions are selected from maleic acid, maleic anhydride or acrylic acid. Even more preferably, the carboxylic acid and/or anhydride functions are selected from maleic anhydride functions.

According to an embodiment, the carboxylic acid- and/or anhydride-modified polyolefin compound(s) C represent from 1 to 20% by weight, preferably from 3 to 15% by weight, more preferably from 5 to 10% by weight, of the total weight of the adhesive composition.

Ingredient C1

By "carboxylic acid- and/or anhydride-modified polyolefin copolymer C1" or "modified polyolefin copolymer C1" it is to be understood a copolymer comprising at least two olefin monomers having a different nature, said polyolefin copolymer is modified with carboxylic acid and/or carboxylic anhydride functions.

For example, the modified polyolefin copolymer C1 may be grafted with carboxylic acid and/or anhydride functions.

According to an embodiment, the modified polyolefin copolymer C1 comprises at least two different olefin monomers having from 2 to 16 carbon atoms, preferably having from 2 to 8 carbon atoms. According to an embodiment, the olefin monomers are alpha-olefins monomers. Preferably, the olefin monomers are selected from ethylene, propylene, butylene, pentene and hexene.

The carboxylic acid- and/or anhydride-modified polyolefin copolymer C1 used in the adhesive composition of the invention has a molecular weight higher than 10000 g/mol, preferably higher than or equal to 20000 g/mol.

The carboxylic acid- and/or anhydride-modified polyolefin copolymer C1 has a density higher than or equal to 0.890 g/cm$^3$, preferably higher than or equal to 0.900 g/cm$^3$, more preferably higher than or equal to 0.910 g/cm$^3$, even more preferably higher than or equal to 0.920 g/cm$^3$, for example higher than or equal to 0.930 g/cm$^3$.

The density of the carboxylic acid- and/or anhydride-modified polyolefin copolymer C1 may be measured according to ASTM D792.

According to the embodiment wherein the modified polyolefin compound C is selected from the modified polyolefin copolymer C1, the adhesive composition has good creep performances both for contact applications and spiral applications.

Among carboxylic acid- and/or anhydride-modified polyolefin copolymers C1 that can be used in the present invention, mention may be made of Amplify® GR 204 (available from Dow Chemical) or Exxelor® PO 1015 (available from ExxonMobil Chemical).

Ingredient C2

By "carboxylic acid- and/or anhydride-modified polyolefin wax C2" or "modified polyolefin wax C2" it is to be understood a wax comprising carboxylic acid and/or carboxylic anhydride functions and at least one olefin compound. According to an embodiment, the modified polyolefin wax C2 used in the adhesive composition consists essentially in olefin monomers and carboxylic acid and/or carboxylic anhydride functions.

By "wax", it is to be understood semi-crystalline polymers that are solid at room temperature and preferably that have a Ring and Ball softening point of from 50° C. to 170° C. They are produced in a wide range of molecular weights, monomers, densities and crystallinity levels. Typical waxes include synthetic waxes such as a Fischer-Tropsch wax; petroleum waxes such as a paraffin wax and a microcrystalline wax, since those waxes comprise olefin units.

The modified polyolefin wax C2 may be obtained according to various reactions. For example, the modified polyolefin wax C2 may be:

a wax obtained by graft reaction of carboxylic acid and/or carboxylic anhydride with a base wax, or a wax obtained by copolymerization of carboxylic acid and/or carboxylic anhydride in case of synthesizing the wax by polymerization.

According to the present invention, the "base wax" is a polyolefin wax, such as polyethylene wax, polypropylene wax, ethylene-propylene copolymer wax, or also synthetic waxes such as Fischer-Tropsch wax; petroleum waxes such as a paraffin wax and a microcrystalline wax.

According to an embodiment of the invention, the modified polyolefin wax C2 is a copolymer comprising at least one olefin monomer and carboxylic acid and/or carboxylic anhydride monomer.

The carboxylic acid- and/or anhydride-modified polyolefin wax C2 has a molecular weight ranging from 100 to 10000 g/mol, preferably from 1000 to 5000 g/mol.

According to an embodiment of the invention, the maleic acid anhydride modified polyolefin wax C2 is selected from ethylene-maleic acid anhydride copolymers and propylene-maleic acid anhydride copolymers.

Among carboxylic acid- and/or anhydride-modified polyolefin wax C2 that can be used in the present invention, mention may be made of AC® 573P, AC® 580 or AC® 596P (available from Honeywell).

According to an embodiment, the adhesive composition comprises two carboxylic acid- and/or anhydride-modified polyolefin compounds C having different molecular weight. Preferably, the adhesive composition comprises a carboxylic acid- and/or anhydride-modified polyolefin copolymer C1 having a molecular weight higher than 10000 g/mol and a carboxylic acid- and/or anhydride-modified polyolefin wax C2 having a molecular weight ranging from 100 to 10000 g/mol. The inventors surprisingly found that the combination of a carboxylic acid- and/or anhydride-modified polyolefin copolymer of high molecular weight with a carboxylic acid- and/or anhydride-modified polyolefin wax of low molecular weight improves the creep performances, in particular for spiral spray applications.

The adhesive composition according to the invention does not comprise amorphous olefin homopolymers or copolymers.

The modified compound C used in the adhesive composition of the invention is preferably semi-cristallin. The unmodified alpha-olefin copolymer B is preferably semi-cristallin. The propylene homopolymer A used in the adhesive composition of the invention is preferably semi-cristallin. Preferably, all the homopolymers and copolymers of the hot-melt adhesive composition of the present invention are semi-crystalline type. Indeed, the semi-crystalline olefin polymers provide cohesive strength to the composition.

The term "semi-crystalline polymer" used herein refers to polymeric materials that contain both crystalline and amorphous regions in the solid state. In the crystalline region, the molecular chains of the polymers are all arranged in ordered three-dimensional arrays whose structure can be fully characterized by their unit cells, the smallest structural unit used to describe a crystal. The amorphous polymers, in contrast, do not have ordered three-dimensional structures in the solid state. Their molecular chains are arranged in a completely random fashion in space.

Semi-crystalline polymers can be easily distinguished from completely amorphous polymers by observing the presence or absence of a melting point (Tm) and the associated enthalpy or heat of melting ($\Delta$Hm) derived from the transformation of the crystalline state to liquid state upon heating. All semi-crystalline polymers exhibit a crystalline melting point as determined by Differential Scanning calorimetry (DSC) or equivalent technique, whereas the melting point is absent for amorphous polymers. Amorphous polymers undergo a transition from a glassy solid to a rubbery elastic state in a narrow temperature range around a glass transition temperature Tg. One should not confuse the glass transition temperature (Tg) with the melting point (Tm). Unlike the melting transition of the crystalline materials, the glass transition of amorphous polymers does not have an enthalpy change ($\Delta$H) associated with it.

Ingredient D

According to an embodiment, the tackifying resin D has a number mean molar mass ranging from 100 Da to 5 kDa, preferably from 500 Da to 4 kDa. According to an embodiment, the tackifier resin D is chosen from:

(i) the polyterpene resins having a softening point, from about 10° C. to 140° C., the latter polyterpene resins are generally obtained by polymerization of terpene hydrocarbons such as mono-terpene (or pinene), in the presence of Friedel-Crafts catalysts, (ii) copolymers and terpolymers of natural terpenes obtained by polymerization of, styrene, alpha-methyl styrene, vinyl toluene, (iii) phenolic-modified terpene resins such as, for example, the resin product resulting from the condensation, in an acidic medium, of a terpene and a phenol, (iv) rosins of natural or modified origin, such as rosin extracted from pine gum, wood rosin extracted from tree roots and their derivatives, hydrogenated, dimerized, polymerized or esterified by monoalcohols or polyols such as glycerol and pentaerythritol;

(v) aliphatic and cycloaliphatic petroleum hydrocarbon resins having Ring and Ball softening points of from about 10° C. to 140° C., the latter resins resulting from the polymerization of monomers consisting primarily of aliphatic or cycloaliphatic olefins and diolefins; also included are the hydrogenated aliphatic and cycloaliphatic petroleum hydrocarbon resins;

(vi) aromatic petroleum hydrocarbons and the hydrogenated derivatives thereof;

(vii) aliphatic/aromatic petroleum derived hydrocarbons and the hydrogenated derivatives thereof.

Mixtures of two or more of the above described tackifying resins may be used for some formulations. Also included are the cyclic or acyclic C5 resins and aromatic modified acyclic or cyclic resins.

The number-average molar masses of the resins can be measured using methods well known to a person skilled in the art, for example by steric exclusion chromatography using polyethylene glycol standard.

Such resins D are commercially available and from those of type (i), (ii), (iii) and (iv) defined above, the following products may be mentioned:

resins of type (i): Dertophene® 1510 available from the company DRT having a number-average molar mass Mn of approximately 870 Da; Dertophene® H150 available from the same company, having a molar mass Mn of approximately 630 Da; Sylvarez® TP 95 available from the company Arizona Chemical having a number-average molar mass Mn of approximately 1200 Da;

resins of type (ii): Norsolene® W100 available from the company Cray Valley, which is obtained by polymerization of alpha-methyl styrene without the action of phenols, with a number-average molar mass of 900 Da; Sylvarez® 510 which is also available from the company Arizona Chemical with a number-average molar mass Mn of approximately 1740 Da, the process of obtaining which also comprises the addition of phenols.

resins of type (iv): Sylvalite® RE 100 which is an ester of rosin and pentaerythritol available from the company Arizona Chemical and having a number-average molar mass Mn of approximately 1700 Da, resin of type (iv): Escorez® 5600 available from Exxon Chemicals which is a hydrogenated dicyclopenadiene resin modified by an aromatic compound having a softening temperature of 100° C. and an Mw of about 980 Da; Escorez® 5400 which is a hydrogenated dicyclopentadiene resin also from Exxon Chemicals with a softening temperature of 100° C.; Wingtack® Extra from Cray-Valley; Regalite® R5100 from Eastman (vi).

According to a preferred embodiment, the tackifying resin D used in the composition of the invention is selected from resins obtained by hydrogenation, polymerization or copolymerization (with an aromatic hydrocarbon) of mixtures of unsaturated aliphatic hydrocarbons having approximately 5, 9 or 10 carbon atoms, originating from petroleum cuts (type (iv, v and vi) defined above).

According to an embodiment, the tackifying resin(s) D represent from 10 to 75% by weight, preferably from 20 to 70% by weight, more preferably from 30 to 65% by weight, even more preferably from 35 to 60% by weight, of the total weight of the adhesive composition. The tackifying resin allows reducing the viscosity of the adhesive composition that allows improving the processability of the adhesive composition.

Other Ingredients

According to an embodiment, the hot-melt adhesive composition further comprises at least one plasticizer. Preferably, the plasticizer represents from 10 to 30% by weight, preferably from 15 to 25% by weight of the adhesive composition.

According to an embodiment, the plasticizer may be chosen from the group which not only includes the usual plasticizing oils, such as mineral, paraffinic and naphthenic oil, but also olefin oligomers and low molecular weight polymers, glycol benzoates, as well as vegetable and animal oil and derivatives of such oils. The petroleum-derived oils that may be employed are relatively high boiling temperature materials containing only a minor proportion of aromatic hydrocarbons. In this regard, the aromatic hydrocarbons should preferably be less than 30%, and more particularly less than 15%, by weight, of the oil. Alternately, the oil may be totally non-aromatic. The oligomers may be polypropylenes, polybutenes, hydrogenated polyisoprene, hydrogenated butadiene, or the like having average molecular weights between about 100 and about 10,000 g/mol. Suitable vegetable and animal oils include glycerol esters of the usual fatty acids and polymerization products thereof. Other plasticizers may be used provided they have suitable compatibility. Nyflex® 222B, a naphthenic mineral oil manufactured by Nynas Corporation, has also been found to be an appropriate plasticizer.

According to an embodiment, the hot-melt adhesive composition further comprises a non-functionalized wax, in particular a wax free of carboxylic acid and/or anhydride functions, such as a polyethylene wax. The non-functionalized wax may have a molecular weight ranging from 100 to 10000 g/mol, preferably from 1000 to 5000 g/mol. Among non-functionalized wax, mention may be made of AC®617, a polyethylene based wax available from Honeywell. Preferably, the non-functionalized wax represents from 0.1 to 5% by weight, preferably from 0.5 to 3% by weight, of the total weight of the adhesive composition.

According to an embodiment, the hot melt adhesive composition further comprises at least one antioxidant. Preferably, the antioxidant represents from 0.1 to 2% by weight, preferably from 0.3 to 1% by weight, of the adhesive composition.

According to an embodiment, the antioxidant may be chosen from high molecular weight hindered phenols and multifunctional phenols, such as sulfur and phosphorus-containing phenols. Hindered phenols are well known to those skilled in the art and may be characterized as phenolic compounds which also contain sterically hindered radicals in close proximity to the phenolic hydroxyl group thereof. In particular, tertiary butyl groups generally are substituted onto the benzene ring in at least one of the ortho positions relative to the phenolic hydroxyl group. The presence of these sterically hindered substituted radicals in the vicinity of the hydroxyl group serves to retard its stretching frequency and correspondingly, its reactivity; this steric hindrance thus providing the phenolic compound with its stabilizing properties. Representative hindered phenols may include:

1,3,5-trimethyl-2,4,6-tris(3-5-di-tert-butyl-4-hydroxy-benzyl)benzene;
pentaerythritoltetrakis-3 (3,5-di-tert-butyl-4-hydroxyphenyl)propionate;
n-octadecyl-3 (3,5-ditert-butyl-4-hydroxyphenyl)propionate;
4,4'-methylenebis(4-methyl-6-tert butylphenol);
4,4'-thiobis(6-tert-butyl-o-cresol);
2,6-di-tert-butylphenol;
6-(4-hydroxyphenoxy)-2,4-bis(n-ocytlthio)-1,3,5-triazine;
2,4,6-tris(4-hydroxy-3,5-di-tert-butyl-phenoxy)-1,3,5-triazine;
di-n-octadecyl-3,5-di-tert-butyl-4-hydroxybenzylphosphonate;
2-(n-octylthio)ethyl-3,5-di-tert-butyl-4-hydroxybenzoate; and sorbitol hexa-(3,3,5-di-tert-butyl-4-hydroxy-phenyl)propionate.

The performance of these stabilizers may be further enhanced by utilizing, in conjunction therewith synergists compounds, such as, for example, thiodipropionate esters and phosphites.

A particularly preferred antioxidant is Irganox® 1010, a tetrakis(methylene(3,5-di-teri-butyl-4-hydroxyhydrocinnamate))methane manufactured by BASF.

According to an embodiment of the invention, the hot-melt adhesive composition comprises, preferably consists essentially in:
at least one propylene homopolymer,
at least one alpha-olefin copolymer,
at least one carboxylic acid- and/or anhydride-modified polyolefin compound,
at least one tackifying resin,
optionally at least one plasticizer,
optionally at least one antioxidant.

According to an embodiment of the invention, the hot-melt adhesive composition comprises, preferably consists essentially in:
at least one propylene homopolymer,
at least one alpha-olefin copolymer,
at least one carboxylic acid- and/or anhydride-modified polyolefin compound,
at least one tackifying resin,
optionally at least one plasticizer,
optionally at least one antioxidant,
optionally at least one non-functionalized wax, such as a polyethylene wax.

According to an embodiment of the invention, the hot-melt adhesive composition comprises, preferably consists essentially in:
from 2 to 40% by weight, preferably from 4 to 30% by weight, more preferably from 5 to 20% by weight, of at least one propylene homopolymer,
from 2 to 40% by weight, preferably from 4 to 30% by weight, more preferably from 5 to 20% by weight, of at least one alpha-olefin copolymer,
from 1 to 20% by weight, preferably from 3 to 15% by weight, more preferably from 5 to 10% by weight, of at least one carboxylic acid- and/or anhydride-modified polyolefin compound,
from 10 to 75% by weight, preferably from 20 to 70% by weight, more preferably from 30 to 65% by weight, of at least one tackifying resin,
optionally from 10 to 30% by weight, preferably from 15 to 25% by weight, of at least one plasticizer,
optionally from 0.1 to 2% by weight, preferably from 0.3 to 1% by weight of at least one antioxidant, based on the total weight of the hot-melt adhesive composition.

According to an embodiment of the invention, the hot-melt adhesive composition comprises, preferably consists essentially in:
- from 2 to 40% by weight, preferably from 4 to 30% by weight, more preferably from 5 to 20% by weight, of at least one propylene homopolymer,
- from 2 to 40% by weight, preferably from 4 to 30% by weight, more preferably from 5 to 20% by weight, of at least one alpha-olefin copolymer,
- from 1 to 20% by weight, preferably from 3 to 15% by weight, more preferably from 5 to 10% by weight, of at least one carboxylic acid- and/or anhydride-modified polyolefin compound,
- from 10 to 75% by weight, preferably from 20 to 70% by weight, more preferably from 30 to 65% by weight, of at least one tackifying resin,
- optionally from 10 to 30% by weight, preferably from 15 to 25% by weight, of at least one plasticizer,
- optionally from 0.1 to 2% by weight, preferably from 0.3 to 1% by weight of at least one antioxidant,
- optionally from 0.1 to 5% by weight, preferably from 0.5 to 3% by weight, of at least one non-functionalized wax, such as a polyethylene wax, based on the total weight of the hot-melt adhesive composition.

According to an embodiment of the invention, the hot-melt adhesive composition comprises, preferably consists essentially in:
- at least one propylene homopolymer,
- at least one alpha-olefin copolymer,
- at least one carboxylic acid- and/or anhydride-modified polyolefin copolymer,
- at least one tackifying resin,
- optionally at least one plasticizer,
- optionally at least one antioxidant.

According to an embodiment of the invention, the hot-melt adhesive composition comprises, preferably consists essentially in:
- from 2 to 40% by weight, preferably from 4 to 30% by weight, more preferably from 5 to 20% by weight, of at least one propylene homopolymer,
- from 2 to 40% by weight, preferably from 4 to 30% by weight, more preferably from 5 to 20% by weight, of at least one alpha-olefin copolymer,
- from 1 to 20% by weight, preferably from 3 to 15% by weight, more preferably from 5 to 10% by weight, of at least one carboxylic acid- and/or anhydride-modified polyolefin copolymer,
- from 10 to 75% by weight, preferably from 20 to 70% by weight, more preferably from 30 to 65% by weight, of at least one tackifying resin,
- optionally from 10 to 30% by weight, preferably from 15 to 25% by weight, of at least one plasticizer,
- optionally from 0.1 to 2% by weight, preferably from 0.3 to 1% by weight of at least one antioxidant,
- based on the total weight of the hot-melt adhesive composition.

According to an embodiment of the invention, the hot-melt adhesive composition comprises, preferably consists essentially in:
- at least one propylene homopolymer,
- at least one alpha-olefin copolymer,
- at least one carboxylic acid- and/or anhydride-modified polyolefin copolymer and
- at least one carboxylic acid- and/or anhydride-modified polyolefin wax,
- at least one tackifying resin,
- optionally at least one plasticizer,
- optionally at least one antioxidant.

According to an embodiment of the invention, the hot-melt adhesive composition comprises, preferably consists essentially in:
- from 2 to 40% by weight, preferably from 4 to 30% by weight, more preferably from 5 to 20% by weight, of at least one propylene homopolymer,
- from 2 to 40% by weight, preferably from 4 to 30% by weight, more preferably from 5 to 20% by weight, of at least one alpha-olefin copolymer,
- from 1 to 20% by weight, preferably from 3 to 15% by weight, more preferably from 5 to 10% by weight, of at least one carboxylic acid- and/or anhydride-modified polyolefin copolymer and at least one carboxylic acid- and/or anhydride-modified polyolefin wax,
- from 10 to 75% by weight, preferably from 20 to 70% by weight, more preferably from 30 to 65% by weight, of at least one tackifying resin,
- optionally from 10 to 30% by weight, preferably from 15 to 25% by weight, of at least one plasticizer,
- optionally from 0.1 to 2% by weight, preferably from 0.3 to 1% by weight of at least one antioxidant,
- based on the total weight of the hot-melt adhesive composition.

According to an embodiment, the adhesive composition of the invention does not comprise styrene block (co)polymers.

Another object of the present invention is a method for manufacturing the hot-melt adhesive composition according to the invention. The adhesive composition of the present invention may be produced using any of the techniques known in the art. A representative example of the procedure may involve placing all of the components, except the tackifier, in a jacketed mixing kettle equipped with rotors, and thereafter raising the temperature of this mixture to a range of 150° C. to 177° C. It should be understood that the precise temperature to be used in this step would depend on the melting point of the particular ingredients. The tackifier may subsequently be introduced to the kettle under agitation and the mixing may be allowed to continue until a consistent and uniform mixture is formed. The contents of the kettle may be protected with inert gas such as carbon dioxide and nitrogen during the entire mixing process.

The resulting hot melt adhesives may then be applied to substrates using a variety of coating techniques. Examples include hot melt slot die coating, hot melt wheel coating, hot melt roller coating, melt blown coating and spiral spray coating. In a preferred embodiment, the hot melt adhesive is sprayed onto a substrate using spiral spray technique, which is a preferred technique to produce a filamentary spiral pattern for diaper construction and elastic attachment. In one example, the coater is equipped with a disc-like coating die which has a nozzle tip in the center. The tip may be surrounded with a series of inclined orifices for hot air to pass through. The hot melt adhesive may be pumped out of the nozzle in the form of a small filament. The filament may then be rotated by high-velocity hot air jets coming out of the orifices, thereby producing a helical pattern from a single strand of adhesive. It is not the intent of this invention to provide a full description of spiral spray technique and the details can be found in the literature.

Another objection of the present invention is the use of a hot-melt adhesive composition as defined in the present invention for binding an elastic material between two separate substrates.

Another object of the present invention is a laminate comprising at least one elastic material and at least two substrates, said elastic material being inserted between two substrates and covered with the hot-melt adhesive composition of the invention.

By "laminate" it is to be understood a multi-layer material, i.e. a material consisting in at least two layers.

A material is typically considered elastic when it is characterized as having a high percent elastic recovery (i.e., a low percent permanent set) after application of a biasing force. Ideally, elastic materials are characterized by a combination of three temperature independent properties, i.e., a low percent permanent set, and a low percent stress or load relaxation. That is, there should be, (1) no or low relaxing of the stress or unloading while the material is stretched, and (2) complete or high recovery to original dimensions after the stretching, biasing or straining is discontinued. Thus, an elastic material is typically a polymer which, free of diluents, has a break elongation in excess of 100% independent of any crimp (when in fiber form) and which when stretched to twice its length, held for one minute, and then released, retracts to less than 1.5 times its original length within one minute of being released. Such polymers include, but are not limited to, natural rubber or synthetic rubbers, segmented polyurethanes (including polyurethaneureas) such as polyetherurethanes and polyesterurethanes, polyetheresters, elastomeric polyethylenes and polypropylenes, and polyetheramides.

According to an embodiment, the elastic material is chosen from elastomeric fiber, tape, film, strip, coating, ribbon and/or sheet, and, substantially linear ethylene polymers.

As examples of elastic material, mention may be made of spandex (e.g., Lycra® spandex and Lycra® XA, a spandex having little or no lubricating finish thereon). In one embodiment, the elastic material comprises spandex or melt spun elastomers. In another embodiment the elastic material comprises natural or synthetic rubbers in the form of fibers or in the form of strips less than about 10 mm wide.

The U.S. International Trade Commission defines spandex as a manufactured fiber in which the fiber-forming substance is a long-chain synthetic polymer comprised of at least 85 percent by weight of a segmented polyurethane. Lycra® spandex is known to exhibit nearly ideal, temperature independent elastic properties.

According to an embodiment, the elastic material(s) is(are) inserted between a first substrate selected from polyolefin films, such as polyethylene or polypropylene films, and a second substrate selected from non-woven materials, such as non-woven polypropylene or non-woven polyethylene.

According to an embodiment, the laminate of the invention comprises at least two, preferably at least three elastic materials inserted between two substrates.

According to an embodiment of the invention, the elastic material is in the form of a strand of elastic, having preferably a linear density ranging from 235 dtx to 1520 dtx.

The laminate according to the invention may be manufactured according to a process well known for the skilled person. Document U.S. Pat. No. 6,967,178 describes an example of process for manufacturing a laminate.

A process for manufacturing the laminate according to the invention comprises the following steps:
providing a first substrate,
providing at least one elastic material,
applying the adhesive composition according to the invention onto at least one elastic material,
contacting the elastic material(s) covered with the adhesive composition with the first substrate,
contacting the second substrate with the elastic material(s).
compression between two rollers.

Preferably, the elastic material is stretched before application of the adhesive composition, preferably such that the length of the elastic ranges from 2 to 4 times its length at rest (i.e. without stretching), ideally the stretching is performed such that the length of the elastic becomes 3 times longer that the length of the elastic at rest.

Preferably, the adhesive composition is applied at a temperature ranging from 140° C. to less than 160° C., preferably at a temperature ranging from 145 to 155° C., ideally at a temperature of approximately 150° C.

Preferably, the compression level of the laminates at the nip rolls is about 1 bar.

According to an embodiment, the adhesive composition has an open time ranging from 0.2 second to 10 seconds, preferably from 0.4 to 5 seconds.

The open time is defined as the time during which the adhesive composition keeps its adhesive properties. In particular, it corresponds to the time between the application of the adhesive composition and the application of the second substrate.

The adhesive composition of the invention may be applied onto the elastic material either by contact applications or by spraying applications.

The contact application uses a contact nozzle from which the adhesive composition is applied onto the elastic material in a straight way. In the case wherein the elastic material is in the form of a strand, the adhesive composition is applied onto the elastic material in a straight way along the strand. If there are several elastic strands in the laminate, the adhesive composition is applied separately onto each strand. A same apparatus may comprise several nozzle in order to apply the adhesive composition simultaneously onto the several elastic strands. An example of process for applying the adhesive composition with a contact application is described in document US 2012/0258246.

FIG. 1A illustrates the case wherein three elastics (1, 1', 1") are covered with the adhesive composition (2, 2', 2") represented by thick lines. The adhesive composition is applied onto each elastic. FIG. 1A represents a cross section of the elastics covered with the adhesive composition.

An example of devices for the contact application is the Allegro® device from Nordson.

According to this embodiment, the adhesive composition is applied at a rate ranging from 100 to 600 m/min. Preferably, the amount of adhesive composition may range from 10 to 100 mg per meter of elastic strand, preferably from 20 to 50 mg/m of elastic strand. Preferably, the amount of adhesive composition is expressed per meter of elastic strand under stretch.

The spiral application comprises the application of the adhesive composition which is extruded from a nozzle, said extruded adhesive composition is deflected by the application of an air flow before application to the elastic material(s). The air deflects the extruded adhesive composition such that said adhesive composition is applied by forming a spiral. If there are several elastic strands in the laminate, the adhesive composition is applied in one step onto several elastic strands. For example, if the laminate comprises three elastic strands, one nozzle may apply simultaneously by spraying application the adhesive composition onto the three strands. It is also possible having more than three strands, such as six or nine strands and in those cases, several nozzles may apply the adhesive composition onto several strands by spiral application.

Figure 1B:
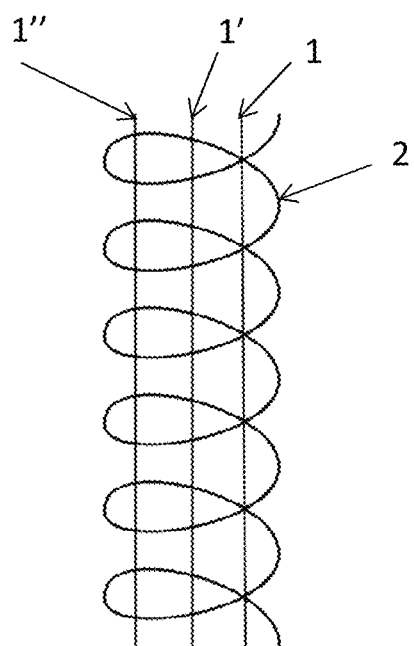
FIG. 1B shows three elastic strands (1, 1', 1'') covered with the adhesive composition according to the invention (2) using a spiral application.

FIG. 1B illustrates the case wherein three elastics (1, 1', 1") are covered with the adhesive composition (2) represented in continuous line. The adhesive composition is applied once onto the three elastics.

According to this embodiment (spiral or spraying application), the adhesive composition is applied at a rate ranging from 100 to 500 m/min. Preferably, the amount of adhesive composition may range from 5 to 100 g/m², preferably from 10 to 50 g/m², even more preferably from 10 to 20 g/m². The amount of adhesive composition is preferably expressed in g per square meter of the substrate onto which the elastic material(s) is contacted.

Contact application is more efficient since the adhesive composition covers all the length of the elastic material. Nevertheless, spiral application is the kind of application that is more often used by industrials. Spiral application requires adhesive compositions having better performances. For example, with spiral application, the adhesive composition should preferably have a low viscosity.

According to an embodiment of the invention, the adhesive composition has a Brookfield viscosity, measured at 149° C., of less than 20000 mPa·s.

There is thus a need to provide adhesive composition that can be applied by contact application and by spiral application.

FIG. 2 illustrates a process for manufacturing the laminate according to the invention:

FIG. 2A represents a first substrate 3, which is preferably a polyolefin film, FIG. 2B represents the elastic materials covered with the adhesive composition of the invention (after spiral application) in contact with the first substrate 3, FIG. 2C represents the laminate of the invention wherein a second substrate 4 has been contact with the elastic materials covered with the adhesive composition.

Another object of the invention is a disposable article comprising the laminate according to the invention.

The disposable article is preferably a disposable hygiene article, preferably chosen from diapers, training pants, absorbent underpants, adult incontinence products, feminine hygiene products, and the like.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding application No. EP 15306702.0, filed Oct. 23, 2015 are incorporated by reference herein.

EXAMPLES

In the following examples, different adhesive compositions have been prepared and their performances have been evaluated.

Preparation of the Compositions

The following products have been used:

Ingredient A:

L-Modu® S901 (available from Idemitsu Chemicals) is a propylene homopolymer having a Softening point of 120° C. according to the ASTM E-28-99.

Ingredient B:

Tafmer® PN2070 (available from Mitsui Chemicals) is a propylene/ethylene/1-butene terpolymer obtained with a metallocene catalyst, having a propylene content of about 71% mol, having a melting point of 140° C. (measured according to ASTM D2117), a density of 0.867 g/cm³ (measured according to ASTM D 1505) and a melt flow rate of 7.0 g/10 min (measured according to ASTM D 1238), Tafmer® PN20300 (available from Mitsui Chemicals) is a propylene/ethylene/1-butene terpolymer obtained with a metallocene catalyst, having a propylene content between 60 and 80% mol, a melting point of 160° C. (measured according to ASTM D2117), a density of 0.868 g/cm³ (measured according to ASTM D 1505) and a melt flow rate of 30.0 g/10 min (measured according to ASTM D 1238), Ingredient C1:

Amplify® GR 204 (available from Dow Chemical) is a maleic anhydride grafted ethylene and 1-hexene copolymer with a melt flow rate of approximately 9-15 g/10 min (ASTM D1238, 190° C./2.16 kg) and a maleic anhydride level of approximately 1-1.4% wt, and having a density of 0.952 g/cm³ (ASTM D792), a Vicat Softening temperature of 121° C. (ASTM D1525) and a melting temperature (measured by DSC) of 127° C., Exxelor® PO 1015 (available from ExxonMobil Chemical) is a maleic anhydride functionalized (1% wt) propylene-ethylene copolymer (ethylene content of about 13% wt), having a weight-average molecular weight of about 210000 g/mol, a density of about 0.900 g/cm³ (ASTM D 792), and a melt flow rate of 22 g/10 min (ASTM D 1238, 190° C./1.2 kg), Ingredient C2:

AC® 573P (available from Honeywell) is an ethylene anhydride maleic copolymer wax with 0.5% wt of maleic anhydride, yielding a saponification number of 5, AC® 580 (available from Honeywell) is an ethylene-acrylic acid (EAA) copolymer wax with an acrylic acid content of about 10% wt, AC® 596P (available from Honeywell) is a propylene maleic anhydride copolymer wax with a saponification number of 50, Ingredient D:
Escorez® 5400 (available from ExxonMobil Chemical) is a hydrogenated cycloaliphatic hydrocarbon resin,
Nyflex® 223 (available from Nynas) is a naphthenic plasticizer oil,
Irganox® 1010 (available from BASF) is an antioxidant,
AC® 617 (available from Honeywell) is a low molecular weight polyethylene homopolymer wax,
Affinity® GA 1000R (available from Dow Chemical) is a maleic anhydride grafted ethylene and octene copolymer having a density of 0.878 g/cm$^3$ (ASTM D 792), a melting temperature (measured by DSC, 10° C./min) of 68° C. and a melt flow rate index of approximately 660 g/10 min (ASTM D 1238, 190° C./2.16 kg),
Affinity® GA 1900 (available from Dow Chemical) is an ethylene and octene copolymer having a density of 0.870 g/cm$^3$ (ASTM D 792), a melting temperature (measured by DSC, 10° C./min) of 68° C. and a melt index of approximately 1000 g/10 min (ASTM D 1238, 190° C./2.16 kg).

Comparative Examples

Control E: Zero Creep Avance® available from Bostik, adhesive composition based on a styrene bloc copolymer (without polyolefins).

Composition F detailed in table 1.
Composition G detailed in table 1.
Composition H detailed in table 1

The comparative compositions F, G and H are indicated in table 1 below and the amount of each ingredient is expressed in percentage by weight based on the total weight of the composition.

TABLE 1 comparative compositions F, G and H

|  | F | G | H |
| --- | --- | --- | --- |
| L-Modu ® S901 (A) | 8.0 | 12.0 | 8.0 |
| Tafmer ® PN2070 (B) | 5.0 | — | — |
| Tafmer ® PN20300 (B) | 7.0 | 7.0 | 6.0 |
| Affinity ® GA 1000 R | — | 2.5 | — |
| Affinity ® GA 1900 | — | — | 6.0 |
| AC ®-617 | 2.0 | — | 2.0 |
| Escorez ® 5400 (D) | 58.5 | 58.0 | 58.5 |
| Nyflex ® 223 | 19.0 | 20.0 | 19.0 |
| Irganox ® 1010 | 0.5 | 0.5 | 0.5 |

Further comparative compositions I and J are indicated in table 1bis below and the amount of each ingredient is expressed in percentage by weight based on the total weight of the composition.

TABLE 1bis comparative compositions I and J

|  | I | J |
| --- | --- | --- |
| L-Modu ® S901 (A) | 8.0 | 20 |
| Tafmer ® PN20300 (B) | 65.5 | 16.8 |
| Amplify ® GR 204 (C1) | 5.0 | 12.1 |
| AC ®-573P (C2) | 2.0 | 4.9 |
| Nyflex ® 223 | 19.0 | 45.7 |
| Irganox ® 1010 | 0.5 | 0.5 |

Examples 1 to 11 according to the invention have been prepared. The compositions 1 to 11 according to the invention are indicated in table 2 below and the amount of each ingredient is expressed in percentage by weight based on the total weight of the composition.

TABLE 2

Compositions 1 to 11

|  | 1 | 2 | 3 | 4 | 5 | 6 | 7 | 8 | 9 | 10 | 11 |
| --- | --- | --- | --- | --- | --- | --- | --- | --- | --- | --- | --- |
| L-Modu ® S901 (A) | 8.0 | 8.0 | 8.0 | 8.0 | 8.0 | 8.0 | 8.0 | 8.0 | 8.0 | 8.0 | 8.0 |
| Tafmer ® PN20300 (B) | 7.0 | 7.0 | 6.0 | 7.0 | 7.0 | 5.0 | 7.0 | 7.0 | 5.0 | 6.0 | 6.0 |
| Tafmer ® PN2070 (B) |  |  |  |  |  |  |  | 5.0 |  |  |  |
| Amplify ® GR 204 (C1) | 5.0 | 5.0 | 6.0 | 5.0 | 5.0 | 5.0 | 5.0 |  | 5.0 | 6.0 | 5.0 |
| Exxelor ® PO 1015 (C1) |  |  |  |  |  |  |  |  | 2.0 |  | 1.0 |
| AC ®-573P (C2) |  |  |  | 2.0 |  |  |  | 2.0 |  |  |  |
| AC ®-580 (C2) |  |  |  |  | 2.0 |  |  |  |  |  |  |
| AC ®-596P (C2) |  |  |  |  |  | 2.0 | 2.0 |  |  | 2.0 | 2.0 |
| Escorez ® 5400 (D) | 58.5 | 58.5 | 58.5 | 58.5 | 58.5 | 58.5 | 58.5 | 58.5 | 58.5 | 58.5 | 58.5 |
| AC ®-617 |  | 2.0 | 2.0 |  |  | 2.0 |  |  | 2.0 |  |  |
| Nyflex ® 223 | 21.0 | 19.0 | 19.0 | 19.0 | 19.0 | 19.0 | 19.0 | 19.0 | 19.0 | 19.0 | 19.0 |
| Irganox ® 1010 | 0.5 | 0.5 | 0.5 | 0.5 | 0.5 | 0.5 | 0.5 | 0.5 | 0.5 | 0.5 | 0.5 |

Compositions F, G, H, J and 1 to 11 have been prepared by mixing the ingredients according to a process as described above in the detailed description of the invention.

It has been observed that comparative composition I could not have been prepared.

Physical Properties of the Compositions

The Brookfield viscosity has been measured at 149° C. and at 163° C. (V(149° C.) and V(163° C.) and is expressed in mPa·s in tables 3 and 3 bis below.

The Softening Point in glycerin has been measured (Sp) and is expressed in ° C. in tables 3 and 3bis below.

The Glass transition temperature (Tg), or the temperature corresponding to the maximum of damping factor (Tangδ), has been measured by Dynamic Mechanical Analysis (DMA) in strain controlled mode (1%) and a temperature ramp of 6° C./min at frequency sweep of 1 Hz and is expressed in ° C. in tables 3 and 3bis below.

TABLE 3

Physical properties of compositions E, F, G, H, J and 1 to 3

|  | E | F | G | H | J | 1 | 2 | 3 |
|---|---|---|---|---|---|---|---|---|
| V(149° C.) | 14000 | >20000 | 9100 | 4700 | >20000 | 10600 | 13200 | 13480 |
| V(163° C.) | 7500 | 8860 | 5150 | 2650 | 60500 | 6830 | 6690 | 6610 |
| Sp | 92.2 | 126.5 | 92.6 | 93 | n.d. | 116 | 116 | 115 |
| Tg | 18.0 | 9.8 | 10.7 | 6.1 | n.d. | 14.2 | 16 | 15.1 | n.d. = not determined

TABLE 3bis

Physical properties of compositions 4 to 11

|  | 4 | 5 | 6 | 7 | 8 | 9 | 10 | 11 |
|---|---|---|---|---|---|---|---|---|
| V(149° C.) | 13350 | 13430 | 8500 | 12700 | 16700 | 11350 | 14900 | 14000 |
| V(163° C.) | 6710 | 6940 | 4520 | 6310 | 9550 | 6250 | 6500 | 6330 |
| Sp | 115 | 115.5 | 116 | 120 | 130 | 126 | 119 | 124.5 |
| Tg | 16 | 15.1 | 15.9 | 15 | 7.5 | 18.6 | 17 | 17 |

We observe that the viscosity at 149° C. of the adhesive compositions 1 to 11 according to the invention is less than 20000 mPa·s. Said low viscosity means that the adhesive composition can be applied to a temperature of 150° C. On the contrary, the viscosity of the comparative composition F is too high to allow its application to a temperature of 150° C. Comparative composition F requires a higher application temperature (160° C. for example).

We also observe that the viscosity of comparative composition J free of tackifying resin cannot be measured at 149° C. and remains very high at 163° C.

Creep Performances
Preparation of the Specimen

Specimens for creep resistance tests were prepared using Nordson Coater CTL4400 by laminating three elastic strands (T837 Lycra Hyfit® Fiber) stretched to 300% between one layer of spunbond polypropylene nonwoven fabric of 14 g/m2 basis weight and breathable PE film of 20 μm thickness. In the case of spiral application, adhesives were spiral sprayed according to coating application methods known in the art, at 15 g/m² coating weight using Nordson spiral nozzle with a 0.2 seconds open time, at a speed laminator rate of 180 m/min and 1 bar compression at the nip rolls. While the adhesive temperature was kept at 150° C. in the melting tank, piping and nozzle and the heated air used for spraying, the air pressure was adjusted for each adhesive to optimize the spiral pattern.

In the case of contact application, laminations were prepared by continuous elastic coating application methods known in the art, using Nordson Allegro nozzle at application temperature 150° C. with add-on level of 30 mg/m/strand at a speed laminator rate of 180 m/min and 1 bar compression at the nip rolls.

Three strands of polyurethane elastic material were contacted with a polyethylene film substrate. These strands were before stretched with a ratio of extension of 1:3. Then the substrate and stretched elastic strands ({substrate+elastic strands}) were run at a speed rate of 180 m/min within an atmosphere of 1 bar and a temperature of 150° C. The adhesive composition is then applied onto the "running" {substrate+elastic strands} using either a contact application (with Allegro® material) or a spiral application.

Then, a non-woven substrate is applied onto the bonded {substrate+elastic strands} in order to obtain a laminated specimen.

When the contact application is used, the amount of adhesive composition applied is of 30 mg/strand/m.

When the spiral application is used, the amount of adhesive composition applied is of 15 g/m².

Implementation of the Creep Test

Creep resistance test was carried out with laminated specimens. The specimen, cut to 300 mm in length was stretched out completely and its ends were securely attached to a piece of rigid corrugated paperboard. A length of 200 mm was marked and the elastic strands were cut at the marks. The specimen was then placed four hours in an air-circulating oven at 38° C. Under these conditions, the elastic strands under stress can retreat to a certain distance. The distance between the ends was measured with a ruler. The ratio of the final length to the initial length, expressed in percentage (%), is defined as the Creep Resistance or bond retention.

The tests have been performed at different instants and temperatures after the preparation of the laminated specimens:

Initial: right after the preparation of the laminated specimens,
2 weeks @ 23° C.: after 2 weeks of storage at 23° C. of the laminated specimens,
2 weeks @ 55° C.: after 2 weeks of storage at 55° C. of the laminated specimens,
4 weeks @ 23° C.: after 4 weeks of storage at 23° C. of the laminated specimens,
4 weeks @ 55° C.: after 4 weeks of storage at 55° C. of the laminated specimens.

Figure 3A:
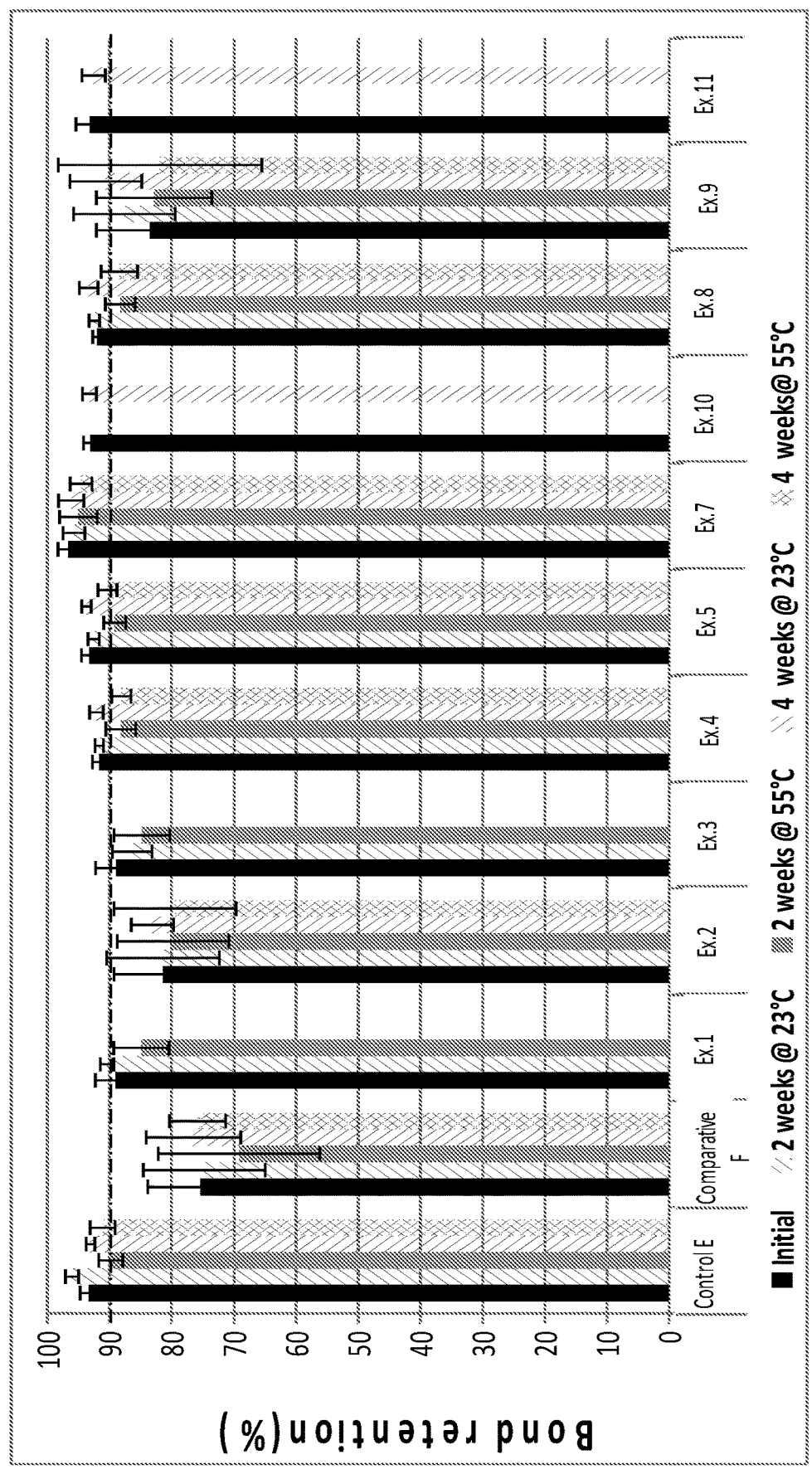
FIG. 3A and FIG. 3B are diagrams illustrating the results of the creep performances of different laminates, said creep test has been performed at different time after the manufacturing of the laminate.
Figure 3B:
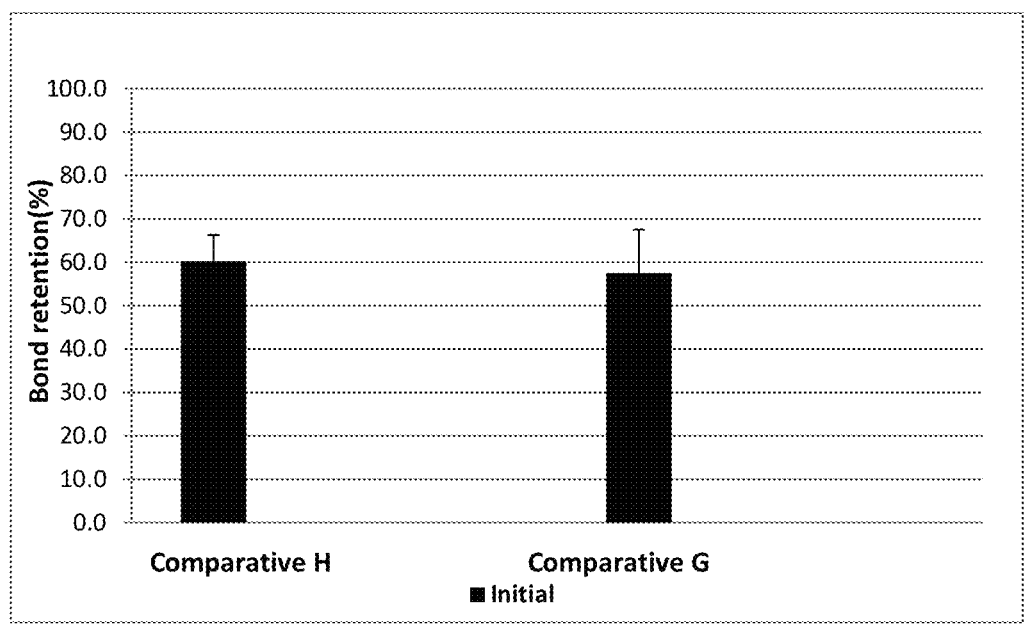
Figure 4A:
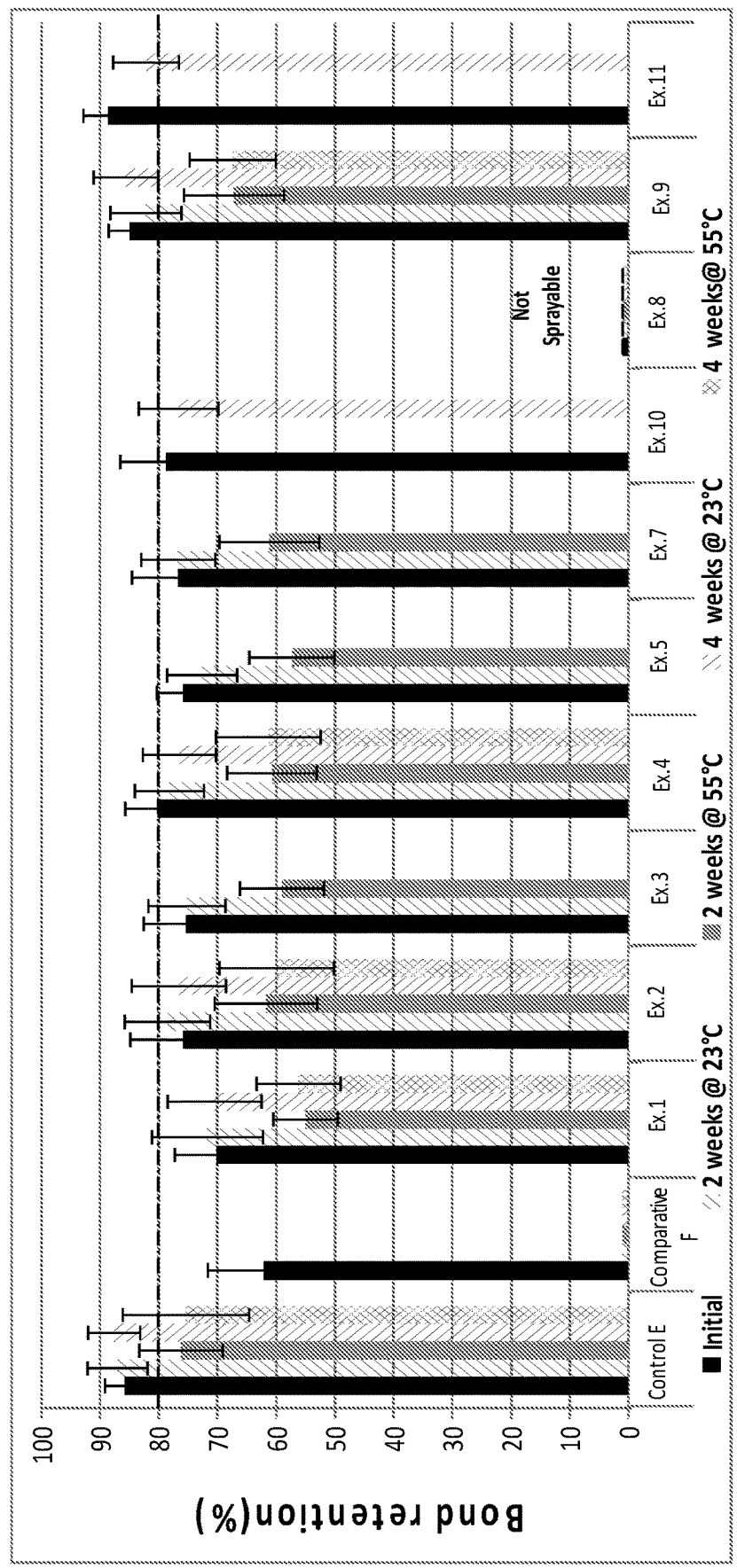
FIG. 4A and FIG. 4B are diagrams illustrating the results of the creep performances of different laminates, said creep test has been performed at different time after the manufacturing of the laminate.
Figure 4B:
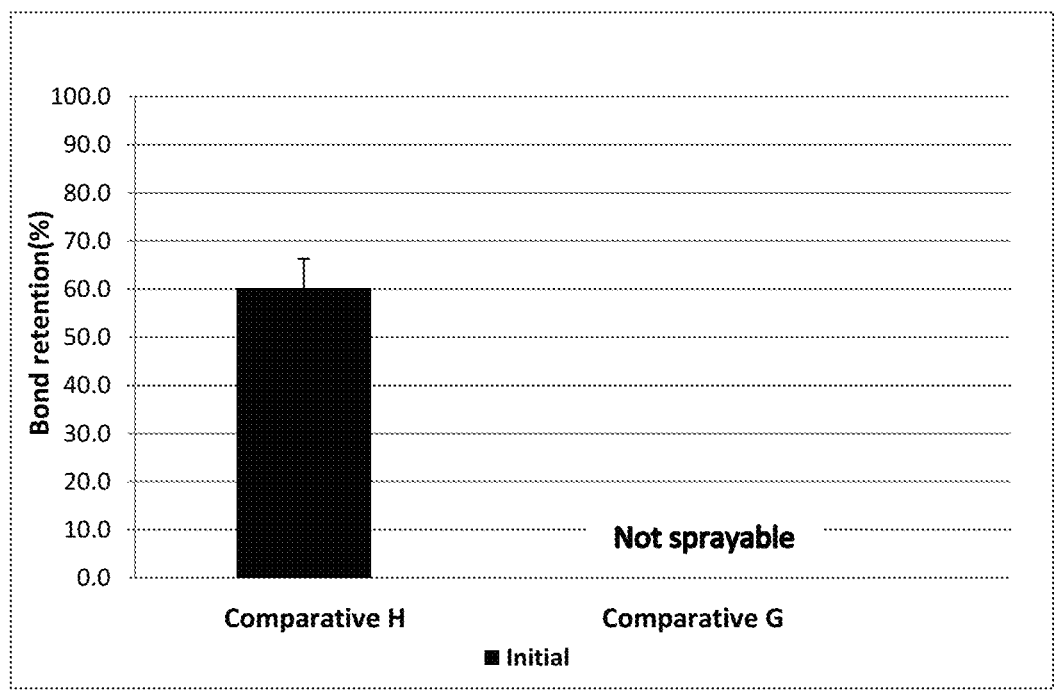

The results of the creep performances are presented in FIGS. 3A and 3B for the contact application and in FIGS. 4A and 4B for the spiral application.

In FIG. 3B, the tested compositions are comparative compositions G and H at initial time. Since the bond retention was not satisfying initially, no further tests have been performed with those comparative compositions.

In FIG. 4B, the tested compositions are comparative compositions G and H at initial time. Nevertheless, comparative composition G cannot be applied using the spiral application. For comparative composition H, since the bond retention was not satisfying initially, no further tests have been performed with this comparative composition.

As shown in FIGS. 3A and 3B, we observe that the comparative compositions F, G and H provide respectively an initial bond retention of about 75%, 58% and 60% whereas the compositions 1 to 11 according to the invention all provide an initial bond retention of at least 80%. In particular, it is preferable when the bond retention is at least equal to 70% after a long period of storage at high temperature for a contact application.

The composition of the adhesive composition 6 is very similar to the composition of the adhesive composition 7 and thus it has not been tested using the Creep test but it is assumed that the adhesive composition 6 will give Creep results that are very similar to the Creep results of the adhesive composition 7.

As shown in FIGS. 4A and 4B, we observe that the comparative compositions F and H provide respectively initial bond retention of about 62% and 60% whereas the compositions 1 to 7 and 9 to 11 according to the invention all provide initial bond retention of at least 70%. In particular, it is preferable when the initial bond retention is at least equal to 70%.

Comparative composition J has a too high viscosity to be processed for the creep test performed at 150° C. and even at a higher temperature of 165° C.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A hot-melt adhesive composition comprising:
   (A) from 2 to 8% by weight of at least one propylene homopolymer,
   (B) from 2 to 20% by weight of at least one alpha-olefin copolymer optionally comprising propylene wherein the density of said alpha-olefin copolymer is higher than or equal to 0.890 g/cm$^3$ when said alpha-olefin copolymer does not comprise polypropylene,
   (C) from 1 to 20% by weight of at least one carboxylic acid- and/or anhydride-modified polyolefin compound selected from:
      (C1) carboxylic acid- and/or anhydride-modified polyolefin copolymer having a molecular weight higher than 10000 g/mol and having a density higher than or equal to 0.890 g/cm$^3$, and
      (C2) carboxylic acid- and/or anhydride-modified polyolefin wax having a molecular weight ranging from 100 to 10000 g/mol,
   (D) from 20 to 75% by weight of at least one tackifying resin,
wherein said hot-melt adhesive composition does not comprise amorphous olefin homopolymers or olefin copolymers.

2. The hot-melt adhesive composition according to claim 1, wherein said composition contains
   (A) from 5 to 8% by weight of said at least one propylene homopolymer,
   (B) from 5 to 20% by weight of said at least one alpha-olefin copolymer,
   (C) from 5 to 10% by weight of said at least one carboxylic acid- and/or anhydride-modified polyolefin compound, and
   (D) from 30 to 65% by weight of said at least one tackifying resin,
   based on the total weight of the hot-melt adhesive composition.

3. The hot-melt adhesive composition according to claim 1, wherein the mass ratio between the at least one propylene homopolymer (A) and the at least one alpha-olefin copolymer (B) is higher than or equal to 0.8.

4. The hot-melt adhesive composition according to claim 1, wherein the at least one alpha-olefin copolymer (B) comprises at least one propylene monomer.

5. The hot-melt adhesive composition according to claim 1, wherein the at least one carboxylic acid- and/or anhydride-modified polyolefin compound (C) comprises at least one monomer selected from propylene and ethylene, and at least one monomer selected from butylene, pentene or hexene.

6. The hot-melt adhesive composition according to claim 1, wherein the at least one carboxylic acid- and/or anhydride-modified polyolefin compound (C) comprises from 0.5 to 10% by weight of carboxylic acid and/or anhydride functions, based on the total weight of the carboxylic acid- and/or anhydride-modified polyolefin compound.

7. The hot-melt adhesive composition according to claim 1, wherein the at least one carboxylic acid- and/or anhydride-modified polyolefin compound (C) is a carboxylic acid- and/or anhydride-modified polyolefin copolymer having a molecular weight higher than 10000 g/mol and a density higher than or equal to 0.890 g/cm$^3$ (C1).

8. The hot-melt adhesive composition according to claim 7, further comprising at least one carboxylic acid- and/or anhydride-modified polyolefin wax having a molecular weight ranging from 100 to 10000 g/mol (C2).

9. A method of binding an elastic material between two separate substrates, comprising contacting an elastic material covered with the adhesive composition according to claim 1 with the first substrate and a second substrate.

10. The hot-melt adhesive composition according to claim 1, wherein said carboxylic acid- and/or anhydride-modified polyolefin copolymer is a maleic anhydride modified ethylene and 1-hexene copolymer or propylene-ethylene.

11. The hot-melt adhesive composition according to claim 1, wherein said composition contains from 5 to 10% by weight of said at least one carboxylic acid- and/or anhydride-modified polyolefin compound C.

12. The hot-melt adhesive composition according to claim 1, wherein said composition contains from 10 to 30% by weight of a plasticizer.

13. A laminate comprising at least one elastic material and at least two substrates, said elastic material being inserted between the two substrates and covered with the hot-melt adhesive composition according to claim 1.

14. The laminate according to claim 13, wherein the adhesive composition is applied in a spiral form onto the elastic material(s).

15. The laminate according to claim 14, wherein the adhesive composition is applied in an amount of from 10 to 50 g/m$^2$.

16. The laminate according to claim 13, wherein one substrate is selected from non-woven materials and a second substrate is selected from polyolefin films.

17. A process for manufacturing the laminate according to claim 13, said process comprising:
provide a first substrate,
providing at least one elastic material,
applying said hot-melt adhesive composition onto said at least one elastic material,
contacting the elastic material(s) covered with the adhesive composition with the first substrate,
contacting the second substrate with the elastic material(s).

18. A disposable hygiene article comprising at least one laminate according to claim 13.

19. A hot-melt adhesive composition having a creep resistance expressed as a percentage of the final length to the initial length of elastic strands under a stress test comprising:
(A) from 2 to 20% by weight of at least one propylene homopolymer,
(B) from 2 to 20% by weight of at least one alpha-olefin copolymer optionally comprising propylene wherein the density of said alpha-olefin copolymer is higher than or equal to 0.890 g/cm$^3$ when said alpha-olefin copolymer does not comprise propylene,
(C) from 1 to 20% by weight of at least one (C1) carboxylic acid- and/or anhydride-modified polyolefin copolymer comprising at least one monomer selected from propylene and ethylene, and at least one monomer selected from butylene, pentene, or hexene, and at least one (C2) carboxylic acid- and/or anhydride-modified polyolefin wax having a molecular weight ranging from 100 to 10000 g/mol,
(D) from 20 to 75% by weight of at least one tackifying resin,
wherein said hot-melt adhesive composition does not comprise amorphous olefin homopolymers or olefin copolymers.

20. A hot-melt adhesive composition comprising:
(A) from 2 to 20% by weight of at least one semi-crystalline propylene homopolymer,
(B) from 2 to 20% by weight of at least one semi-crystalline alpha-olefin copolymer optionally comprising propylene wherein, the density of said alpha-olefin copolymer is higher than or equal to 0.890 g/cm3 when said alpha-olefin copolymer does not comprise polypropylene,
(C) from 1 to 20% by weight of at least one semi-crystalline carboxylic acid- and/or anhydride-modified polyolefin compound selected from:
(C1) carboxylic acid- and/or anhydride-modified polyolefin copolymer having a molecular weight higher than 10000 g/mol and having a density higher than or equal to 0.890 g/cm$^3$, and
(C2) carboxylic acid- and/or anhydride-modified polyolefin wax having a molecular weight ranging from 100 to 10000 g/mol,
(D) from 20 to 75% by weight of at least one tackifying resin,
wherein said hot-melt adhesive composition does not comprise amorphous olefin homopolymers or olefin copolymers.

* * * * *